United States Patent [19]

Bamfield et al.

[11] 4,022,795
[45] May 10, 1977

[54] METHOD FOR DEHALOGENATING AROMATIC COMPOUNDS

[75] Inventors: Peter Bamfield; Peter Michael Quan, both of Manchester, England

[73] Assignee: Imperial Chemical Industries Limited, London, England

[22] Filed: Aug. 19, 1975

[21] Appl. No.: 605,890

[30] Foreign Application Priority Data

Sept. 17, 1974 United Kingdom ............. 40420/74
May 15, 1975 United Kingdom ............. 20618/75

[52] U.S. Cl. .......................... 260/296 D; 260/578; 260/590 R; 260/668 R
[51] Int. Cl.² ...................................... C07D 401/04

[58] Field of Search .......... 260/296 D, 578, 668 R, 260/590 R

[56] References Cited
UNITED STATES PATENTS 1,227,144  4/1971  Starks et al. ................... 260/465 R

*Primary Examiner*—Alan L. Rotman
*Attorney, Agent, or Firm*—Cushman, Darby & Cushman

[57] ABSTRACT

Dehalogenation of water-immiscible or sparingly soluble aromatic compounds containing chlorine or bromine by contacting with an aqueous solution of a formic acid salt in presence of a hydrogenation catalyst and a surface active agent.

13 Claims, No Drawings

METHOD FOR DEHALOGENATING AROMATIC COMPOUNDS

This invention relates to a process for dehalogenating aromatic (including heteroaromatic) compounds.

According to the invention a process for dehalogenating a water immiscible or sparingly soluble aromatic (including hetero aromatic) compound containing at least one chlorine or bromine atom as a nuclear substituent comprises contacting the said compound with an aqueous solution of a formic acid salt in presence of a hydrogenation catalyst and a surface active agent.

By the term surface active agent we mean any substance which, when dissolved in water lowers its surface energy. We include anionic surface active agents, for example water-soluble salts (e.g. sodium salts) of long chain carboxylic acids or sulphate esters, cationic surface active agents for example quaternary ammonium salts of long chain amines, and non-ionic surface active agents for example polyalkenoxy derivatives of phenols and amines. Such surface active agents include the substances to which the terms "detergent" and "wetting agent" are more commonly applied. Anionic surface active agents, particularly sodium diisopropylnaphthalene sulphates, are especially useful.

Desirably, but not necessarily the surface active agent may be a phase transfer catalyst. By this we mean a substance which promotes reactions by transferring a reactant from an aqueous phase to a non-aqueous phase where it undergoes reaction, thus releasing the phase transfer catalyst for return to the aqueous phase for re-use. Phase transfer catalysts are further discussed for example in UK Patent Specification No. 1,227,144. In the present process the preferred phase transfer catalyst is a quaternary ammonium or phosphonium salt which may be represented by the formulae:

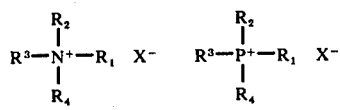

wherein R, $R_2$, $R_3$ and $R_4$ represent alkyl ($C_1 - C_{16}$), aryl, aralkyl, hydroxyalkyl ($C_1 - C_{16}$) or alkoxyalkyl ($C_1 - C_{16}$). One of these R groups may be a linking group between two such quaternary sites. X is one of the ions F, Cl, Br, OH, $SO_4$, $HSO_4$, $SO_3$, $HSO_3$.

As examples of water immiscible or sparingly water soluble aromatic and hetero aromatic compounds containing at least one chlorine or bromine atom as a nuclear substituent we mention for example chlorobenzene, bromobenzene, 1-chloro-2-nitrobenzene, 5-chloro-2-aminobenzotrifluoride, 2,5-dichloronitrobenzene, 2-chloropyridine, 4-chloropyridine, 4-bromo-2,6-dimethylaniline, 1-chloronaphthalene, 1,2-dichlorobenzene, 4-bromobiphenyl and 2,6-difluoro-4-bromoaniline.

In general as well as chlorine or bromine atoms the aromatic and heteroaromatic compounds may contain for example as additional substituents alkyl, aryl, aralkyl, amino, alkyl-arylamino, nitro, carboxylic ester, sulphone, hydroxy, alkoxy, cyano, sulphonamide, carbonamide, or fluoro.

The process of the invention may be used to remove chlorine or bromine atoms without removing fluorine atoms.

The formic acid salt is preferably an alkali metal salt. It may be used as an aqueous solution of any strength but is preferably used as a saturated solution. The pH of the reduction medium may be adjusted as desired by the addition of either an acid, preferably formic acid, or an alkali for example sodium hydroxide or carbonate.

The hydrogenation catalysts which can be used are preferably those based on nickel, palladium, platinum or ruthenium. Excellent results are obtained using palladium-on-carbon.

The reaction is carried out conveniently at temperatures up to 150° C. Operating at atmospheric pressure, temperatures of 75°-110° C are effective, but the temperature range 85°-102° C is usually to be preferred. In those cases where the compound to be dehalogenated is normally solid at the desired reaction temperature a solvent inert to the reaction conditions such as toluene or xylene in which the compound is soluble may be added to provide a second liquid phase.

If desired the reaction may be carried out in the presence of an inert gas such as nitrogen.

Surprisingly we have found that according to the reaction conditions selected a chlorine or bromine atom may be replaced by hydrogen in a process of reductive dehalogenation, or instead of a reductive dehalogenation two or more aromatic or heteroaromatic nuclei may be joined together by carbon to carbon bonds at the positions formerly occupied by nuclear chlorine or bromine atoms. For example from monochloro- or monobromo-benzenes biphenyl may be obtained instead of benzene by suitable choice of reaction conditions.

Reductive dehalogenation i.e., a replacement of a chlorine or bromine atom by a hydrogen atom is favoured by use of an excess of formic acid salt, i.e., greater than 3 mole equivalents, and a pH near to neutrality. On the other hand the portionwise addition of from 1.0 –3.0 mole equivalents of formic acid salt for each chlorine or bromine atom present as nuclear substituent favours the formation of inter nuclear bonds especially under strongly alkaline conditions.

Where reducible groups such as nitro groups are present together with halogen atoms they may be reduced in the course of the reaction.

The process of the invention is useful for example in the manufacture of dyestuff intermediates.

The invention is illustrated but not limited by the following Examples in which parts are by weight.

EXAMPLE 1

Benzyltriethylammonium chloride (1.0 parts), 3% palladium-on-charcoal (50% paste; 6.0 parts) and 1-chloro-2-nitrobenzene (15.8 parts) and sodium hydroxide liquor (32%; 13.5 parts) are charged into a solution of sodium formate (75 parts) in water (150 parts). The mixture is stirred rapidly and then heated to the boil. After holding at the boil under reflux for 3 hours the mixture is steam distilled. Work up of the steam distillate gives 7.7 parts of aniline (83%).

When the above procedure is repeated in absence of benzyltriethylammonium chloride a yield of only 27.5% of aniline is obtained.

EXAMPLE 2

To a solution of sodium formate (38 parts) in water (100 parts) are added sodium hydroxide liquor (32%; 13.5 parts), benzyl triethylammonium chloride (1.0 parts), 3% palladium on charcoal (50% paste; 6.0 parts) and 5-chloro-2-aminobenzotrifluoride (19.6 parts). The mixture is stirred rapidly at the boil under reflux for 4 hours and then steam distilled. The distillate is extracted with chloroform (2 × 50 parts), the extract dried over magnesium sulphate and then the solvent removed to give 9.7 parts (60.3%) of 2-aminobenzotrifluoride.

When the above procedure is repeated in absence of benzyltriethylammonium chloride the yield of 2-aminobenzotrifluoride falls to 23%.

EXAMPLE 3

2,5-Dichloronitrobenzene (19.2 parts) is reduced using the same conditions and quantities in Example 1, giving 6.2 parts (66.8%) of aniline.

EXAMPLE 4

Bromobenzene (15.7 parts), cetyltrimethylammonium bromide (4.0 parts), 3% palladium on charcoal (50% paste; 2.0 parts), sodium formate (6.8 parts) and sodium hydroxide liquor (32%; 27 parts) in water (60 parts) are stirred at the boil under reflux for 4 hours. Sodium formate (6.8 parts) is then added and the mixture held at the boil under reflux for a further 18 hours. The mixture is then steam distilled. The steam distillate is extracted with chloroform (3 × 50 parts) and then the extract dried over anhydrous magnesium sulphate. After filtering off the drying agent the solvent is removed under vacuum to give 5.1 parts (66.2%) of biphenyl.

EXAMPLE 5

Chlorobenzene (11.3 parts) is reduced using the same conditions and quantities in Example 4, giving 3.7 parts (48.1%) of biphenyl.

EXAMPLE 6

2-Chloropyridine (22.7 parts), benzyltriethylammonium chloride (8.0 parts), 3% palladium on charcoal (50% paste; 4.0 parts), sodium formate (20.4 parts) and sodium hydroxide liquor (32%; 27 parts) in water (60 parts) stirred at the boil under reflux for 4 hours. Sodium formate (6.8 parts) is then added tha the mixture held at the boil under reflux for a further 24 hours. The reaction mixture is cooled and then filtered. The residue is washed with ether (75 parts) and then the filtrate extracted with ether (2 × 70 parts). The combined ether extracts are dried over anhydrous magnesium sulphate. After removal of the drying agent the ether is distilled off. The residue is distilled under vacuum and the fraction b.pt. 150°–154°C/20 mm is collected giving 8.1 parts (51.9%) of 2,2'-bipyridyl.

EXAMPLE 7

4-Chloropyridine (11.35 parts), benzyltriethylammonium chloride (2.0 parts), sodium hydroxide liquor (32%; 13.5 parts), 3% palladium on charcoal (50% paste; 2.0 parts) and sodium formate (10.2 parts in water (30 parts) are stirred at the boil under reflux for 4 hours. Sodium formate (3.4 parts) is added and then the mixture held at the boil for a further 24 hours. The reaction mixture is cooled and then filtered. The residue is extracted continuously with hot methanol (100 parts) for 6 hours. The extract when evaporated to dryness gives 3.6 parts (46.2%) of 4,4'-bipyridyl.

EXAMPLE 8

4-Bromo-2,6-dimethylaniline (24.0 parts), 3% palladium on charcoal (50% paste; 2.0 parts), cetyltrimethylammonium bromide (4.0 parts), sodium hydroxide liquor (32%; 13.5 parts), sodium formate (6.8 parts) in water (60 parts) are stirred at the boil under reflux for 3 hours. Sodium formate (6.8 parts is then added and the mixture boiled for 3 hours when a further charge of sodium formate (6.8 parts) is made. The reaction mixture is then held at the boil under reflux for a further 23 hours. The mixture is then steam distilled and from the distillate 2.2 parts (18.2%) of 2,6-dimethylaniline is recovered by extraction with ether. The reaction mixture after steam distillation is cooled to room temperature and then filtered. The residue is extracted continuously with methanol (60 parts) for 5 hours and then the extract cooled. The colourless crystalline precipitate is filtered off and dried to give 7.7 parts (63.3%) of 3,3',5,5'-tetramethyl benzidine.

EXAMPLE 9

18.7 parts of 4-bromoanisole, 6.8 parts of sodium formate, 64 parts of sodium hydroxide liquor (32%), 60 parts of water, 4 parts of cetyl trimethyl ammonium bromide and 3% palladium-on-charcoal (62% paste, 2 parts) are stirred and heated under reflux for 4 hours. A further 6.8 parts of sodium formate are added, and stirring and heating is continued for a further 18 hours. Steam is then passed through the reaction mixture to remove anisole, and the mixture is cooled and filtered. The filter cake is washed with water, dried at 60°, and extracted with 200 parts of chloroform. The palladium catalyst is recovered by filtration of the chloroform extract, and the chloroform is then distilled under vacuum. The white solid residue is triturated with 500 parts of cold water, collected by filtration, and dried at 60°. 5.2 parts of 4,4'-dimethoxybiphenyl, m.p. 172°–173° are obtained.

EXAMPLE 10

Example 9 is repeated, except that the 18.7 parts of 4-bromoanisole are replaced by 12.7 parts of p-chlorotoluene. 5.0 parts of 4,4'-dimethylbiphenyl m.p. 118°–121° are obtained.

EXAMPLE 11

Example 9 is repeated, except that the 18.7 parts of 4-bromoanisole are replaced by 12.7 parts of m-chlorotoluene. In this case the product is somewhat volatile in steam, and is largely recovered from the steam distillate. 3.2 parts of 3,3'-dimethylbiphenyl which is a colourless oil, are obtained.

EXAMPLE 12

This Example illustrates the use of a phosphonium salt as phase transfer catalyst.

Example 4 is repeated except that the 4.0 parts of cetyl trimethyl ammonium bromide are replaced by 4.0 parts of cetyl tributyl phosphonium bromide, and 64 parts of 32% sodium hydroxide liquor are used, and the 60 parts of water are omitted. 4.62 parts of biphenyl are obtained.

EXAMPLE 13

Example 4 is repeated, except that 64 parts of 32% sodium hydroxide liquor are used. 5.36 parts of biphenyl (69.6% yield) m.p. 66°–68°, are obtained.

EXAMPLE 14

The reaction is carried out as in Example 9 except that the 18.7 parts of 4-bromoanisole are replaced by 23.3 parts of 4-bromobiphenyl, and 110 parts of xylene are added as a solvent. After the reflux period, the reaction mixture is not steam distilled, but is cooled, and the solids present are collected by filtration, and washed on the filter with water and with 200 parts of toluene. The filter cake is dried, transferred to a Soxhlet extractor and continuously extracted for 96 hours with 100 parts of boiling dimethyl formamide. Quaterphenyl crystallises when the dimethyl formamide is cooled, and is collected and dried. 7.3 parts of quaterphenyl, m.p. 313°–317° are thereby obtained.

EXAMPLE 15

A mixture comprising 4 parts of sodium diisopropyl naphthalene sulphonate, 1.2 parts of 3% palladium on carbon catalyst, 20 parts of sodium hydroxide, 80 parts of water, 6.8 parts of sodium formate and 15.7 parts of bromobenzene is stirred and heated for 4 hours under reflux. The mixture is then allowed to cool to 90°, a further charge of 6.8 parts of sodium formate is added, and the mixture is reheated and stirred under reflux for a further 16 hours. The mixture is then steam distilled until 800 parts of distillate are collected. The distillate is extracted with chloroform and the chloroform solution, is shown by gas chromatography to contain benzene and biphenyl but no bromobenzene. The chloroform solution is then concentrated by distillation, yielding 5.01 parts of biphenyl, melting at 69°–70°.

EXAMPLE 16

A mixture comprising 20 parts of sodium diisopropyl naphthalene sulphonate, 34 parts of sodium formate, 6 parts of 3% palladium on carbon catalyst, 100 parts of sodium hydroxide, 400 parts of water and 100 parts of 2,6-dimethyl-4-bromoaniline is stirred and heated for 4 hours under reflux. The mixture is allowed to cool to 90°, a second charge of 34 parts of sodium formate is added, and the mixture is reheated and stirred under reflux for 3 hours. A third charge of 34 parts of sodium formate is added in similar fashion and stirring under reflux is continued for a further 16 hours. The mixture is then steam distilled to remove 2,6-dimethylaniline which is formed as a by product and which may be recovered from the distillate. The involatile residue from the steam distillation is cooled and filtered and the filter cake is washed with 100 parts of water and then triturated in 400 parts of boiling methanol. The methanol solution is filtered and allowed to cool when 29.2 parts of 3,5,3′,5′-tetramethyl benzidine are precipitated as white crystals, m.p. 168°–169.5°. A second crop of 1.4 parts m.p. 167°–168° is obtained by concentrating the methanol solution to 100 parts.

EXAMPLE 17

The procedure of Example 15 is repeated, except that the 4 parts of sodium diisopropyl naphthalene sulphonate are replaced by 4 parts of a non-ionic surfactant prepared by condensing cetyl alcohol with 17 moles of ethylene oxide. Again all the bromobenzene is reduced, but a higher proportion of benzene is formed, so that only 4.0 parts of biphenyl are isolated.

EXAMPLE 18

The procedure of Example 15 is repeated except that the 4 parts of sodium diisopropyl naphthalene sulphonate are replaced by 4 parts of sodium dodecylbenzene sulphonate. Again all the bromobenzene is reduced, but mainly to benzene, so that only 0.94 parts of biphenyl are isolated.

COMPARATIVE EXAMPLE

The procedure of Example 15 is repeated except that no surface active agent is used. Reduction is incomplete and the product finally obtained by concentration of the chloroform solution (4.9 parts) is shown by gas chromatography to comprise about equal parts by weight of bromobenzene and biphenyl.

EXAMPLE 19

The procedure of Example 16 is repeated, except that the 20 parts of sodium diisopropyl naphthalene sulphonate are replaced by 20 parts of sodium dodecylbenzene sulphonate. 20.2 parts of 2,6-dimethylaniline and 31.25 parts of 3,5,3′,5′-tetramethylbenzidine, m.p. 168°–170° are obtained.

EXAMPLE 20

The procedure of Example 15 is repeated except that the 15.7 parts of bromobenzene are replaced by 17.1 parts of 2-bromotoluene. 3.01 parts of 2,2′-dimethylbiphenyl are obtained as a colourless oil which is shown to be pure by gas chromatography.

EXAMPLE 21

Reaction is carried out as in Example 15, except that the 15.7 parts of bromobenzene are replaced by 19.9 parts of 4-bromoacetophenone. After steam distillation the distillate is discarded, but the involatile solid residue from the steam distillation is collected by filtration and extracted with chloroform (200 parts). The chloroform suspension is filtered and the chloroform is distilled under reduced pressure. Recrystallisation of the residue from a mixture of toluene and petroleum ether (b.p. 60°–80°) yields 4.54 parts of 4,4′-diacetylbiphenyl, m.p. 185°–186°.

We claim:

1. A process for removing chlorine or bromine atoms without removing fluorine atoms from a compound selected from the group consisting of chlorobenzene, bromobenzene, 1-chloro-2-nitrobenzene, 5-chloro-2-aminobenzotrifluoride, 2,5-dichloronitrobenzene, 2-chloropyridine, 4-chloropyridine, 4-bromo-2,6-dimethylaniline, 1-chloronaphthalene, 1,2-dichlorobenzene, 4-bromobiphenyl and 2,6-difluoro-4-bromoaniline which comprises contacting said compound with an aqueous solution of a formic acid salt in the presence of a palladium-on-carbon hydrogenation catalyst and a surface active agent selected from the class consisting of water soluble salts of long chain carboxylic acids and sulphate esters, sodium diisopropylnaphthalene sulphonate, quaternary ammonium salts of long chain amines and polyalkenoxy derivatives of phenols and amines.

2. Process according to claim 1 wherein the surface active agent is anionic.

3. Process according to claim 2 wherein the surface active agent is sodium diisopropylnaphthalene sulphonate.

4. Process according to claim 1, wherein the surface active agent is a phase transfer catalyst to promote the dehalogenation by transferring reactant from the aqueous phase to the non-aqueous phase.

5. Process according to claim 4 wherein the phase transfer catalyst is a quaternary ammonium salt of the formula

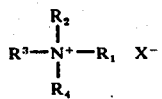

wherein $R_1$, $R_2$, $R_3$ and $R_4$, which may be the same or different, represent alkyl ($C_1$ to $C_{16}$), monocyclic aryl, benzyl, hydroxyalkyl ($C_1$ to $C_{16}$) or alkoxyalkyl ($C_1$ to $C_{16}$) radicals, and X represents one of the ions F, Cl, Br, OH, $SO_4$, $HSO_4$, $SO_3$ or $HSO_3$.

6. Process according to claim 4 wherein the phase transfer catalyst is a quaternary phosphonium salt of the formula

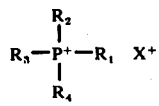

wherein $R_1$, $R_2$, $R_3$ and $R_4$, which may be the same or different, represent alkyl ($C_1$ to $C_{16}$), monocyclic aryl, benzyl, hydroxyalkyl ($C_1$ to $C_{16}$) or alkoxyalkyl ($C_1$ to $C_{16}$) radicals, and X represents one of the ions F, Cl, Br, OH, $SO_4$, $HSO_4$, $SO_3$ or $HSO_3$.

7. Process according to claim 1 wherein the formic acid salt is an alkali metal salt.

8. Process according to claim 1 wherein the catalyst is palladium-on-carbon.

9. Process according to claim 1 carried out at a temperature up to 150° C.

10. Process according to claim 9 carried out at a temperature of 75°–110° C.

11. Process according to claim 9 carried out at a temperature of 85°–102° C.

12. Process according to claim 1 wherein at least 3 mole equivalents of formic acid salt are used and the pH is near to neutrality, whereby to effect replacement of the said chlorine or bromine atom by a hydrogen atom.

13. Process according to claim 1 wherein from 1 to 3 mole equivalents of formic acid salt is added portionwise under strongly alkaline conditions to effect linkage of two aromatic nuclei at the positions formerly occupied by the said chlorine or bromine atoms.

* * * * *